United States Patent [19]
Caiozza et al.

[11] Patent Number: 5,396,280
[45] Date of Patent: Mar. 7, 1995

[54] ANALOG VIDEO PROCESSING APPARATUS AND METHOD FOR ELIMINATING BACKGROUND LEVELS IN THE ANALOG SIGNAL

[75] Inventors: Vincent Caiozza, Endicott; Donald H. Canfield, Vestal; Todd C. Fellows; Norman E. Rittenhouse, both of Endicott; Peter J. Yablonsky, Apalachin, all of N.Y.

[73] Assignee: International Business Machines, Corporation, Armonk, N.Y.

[21] Appl. No.: 23,768

[22] Filed: Feb. 26, 1993

[51] Int. Cl.$^6$ ............................................. H04N 7/18
[52] U.S. Cl. ...................................... 348/126; 348/241
[58] Field of Search ............................ 348/125–130, 348/133, 164, 241, 618, 622; 250/571, 572; H04N 7/18

[56] References Cited

U.S. PATENT DOCUMENTS

| | | | |
|---|---|---|---|
| 3,869,698 | 3/1975 | Trost et al. | 340/146.3 |
| 4,152,723 | 5/1979 | McMahon et al. | 348/126 |
| 4,234,867 | 11/1980 | Butin | 340/146.3 |
| 4,247,873 | 1/1981 | Decuyper | 358/282 |
| 4,446,486 | 5/1984 | Itoh | 358/280 |
| 4,454,539 | 6/1984 | Fedde et al. | 348/126 |
| 4,539,600 | 9/1985 | Takahashi et al. | 358/282 |
| 4,626,922 | 12/1986 | Saitoh | 358/282 |
| 4,644,410 | 2/1987 | Schlichtig | 352/282 |
| 4,691,239 | 9/1987 | Nelson et al. | 358/282 |
| 4,712,010 | 12/1987 | Alm | 348/164 X |
| 4,724,481 | 2/1988 | Nishioka | 250/572 X |
| 4,903,143 | 2/1990 | Sakamoto | 358/457 |
| 4,970,605 | 11/1990 | Fogaroll et al. | 358/461 |

*Primary Examiner*—Victor R. Kostak
*Attorney, Agent, or Firm*—William H. Steinberg; Richard M. Goldman

[57] ABSTRACT

An optical inspection system is provided in which the background video component of an analog video source which limits imaging integrity is removed enhancing the system's ability to process a wider range of image sources with increase digitizing sensitivity. The overall effects of background and background variations are nulled stabilizing the effective signal to noise ratio, thereby increasing inspection capability of the system and improving the system's process window for effective and efficient inspection.

2 Claims, 6 Drawing Sheets

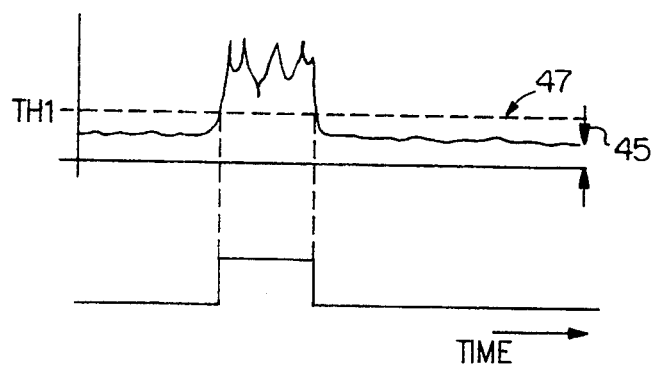
FIG. 3A
FIG. 3B
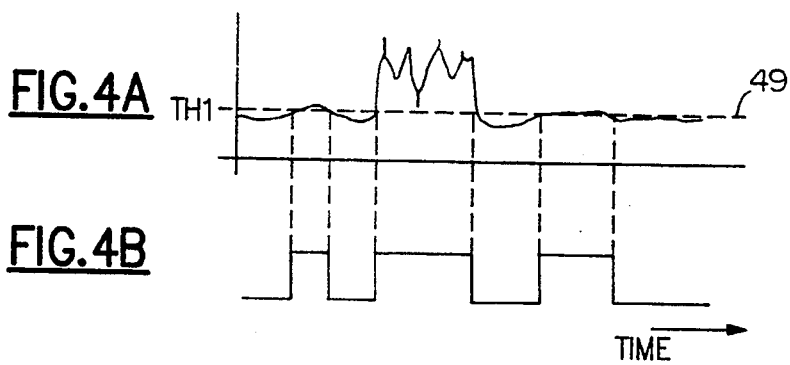
FIG. 4A
FIG. 4B
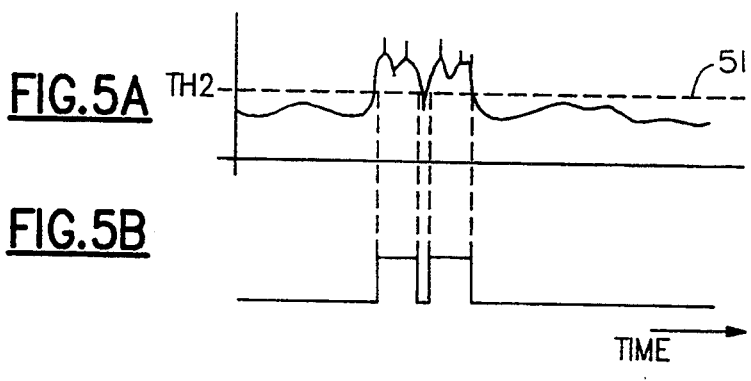
FIG. 5A
FIG. 5B
FIG. 9A
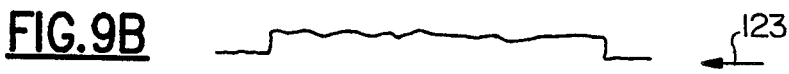
FIG. 9B
FIG. 9C
FIG. 9D

TIME →

ANALOG VIDEO PROCESSING APPARATUS AND METHOD FOR ELIMINATING BACKGROUND LEVELS IN THE ANALOG SIGNAL

BACKGROUND OF THE INVENTION

The present invention relates to automated optical inspection and more particularly to pre-processing of an analog image signal prior to determining digitizing thresholds.

In automated optical inspection applications which entail an analog video source and some form of digital image processing, the analog video signal representing the image source must be converted to digital form by some type of analog-to-digital conversion process. One limitation of the efficiency of this process is determined by the amount of background level in the analog signal as a result of the reflectivity and color of the background of the image source. The reflectivity and color of the background may also vary across any given image source. The "white" and "black" levels of the analog signal correspond to the reflective and non-reflective surface areas of the image plane. This background component, referred to as the "black" level when the "white" level represents the pertinent information, can introduce inaccuracies in the digital signal resulting in a reduced "process window" limiting the defects which can be detected and can result in the need to alter the digitizing sensitivity which requires operator intervention.

Previous techniques of dealing with background levels are 1) determining a minimum digitizing sensitivity below which will be assumed and processed as background, or 2) by using a peak detecting process which is an averaging function rather than a real time or nulling function. These peak values were then used to set a digitizing threshold rather than alter the video signal.

It is an object of the present invention to provide analog video processing method and apparatus which enhances the signal-to-noise ratio of the analog signal and therefore increase the digitizing sensitivity.

It is an object of the present invention to provide analog video processing method and apparatus suitable for use in detecting defects in a wide variety of printed circuit boards including those having multiple layers.

SUMMARY OF THE INVENTION

In one aspect of the present invention an analog video processing circuit for removing background levels is provided. A video buffer means is coupled to an analog video signal for providing a buffered analog video signal. Level detecting means coupled to the output of the video buffer means, includes means for comparing the buffered analog signal to a reference level and providing an output signal when the buffered analog signal exceeds the reference level. A video switch control coupled to the output of the level detecting means for closing the controllable switch means when the buffered analog video signal does not exceed the reference level and opening the controllable switch means when the buffered analog signal does exceed the reference level is provided. Track and hold means coupled through the controllable switch means to the buffered analog video signal tracks the buffered video signal when connected thereto by the controllable switch means and holds the last value when disconnected therefrom by the controllable switch means so that a background signal is developed. Summation means coupled to the track and hold means and to the video buffer, subtracts a signal proportional to the background signal from the buffered analog video signal to obtain a processed analog the video signal.

In another aspect of the present invention a method of eliminating background levels from an analog video signal in an optical inspection system is provided. The analog video signal is tracked and held when its magnitude is below a reference level to determine a background level. A signal proportional to the background level being tracked is subtracted from the analog video signal and the analog video signal with the background level removed is digitized.

BRIEF DESCRIPTION OF THE DRAWING

FIGS. 3A and 3B show a raw analog signal of an inspection area having a low background component, i.e. a high contrast ratio and the corresponding digitized signal, respectively, on a common time scale.

FIGS. 4A and 4B show a raw analog signal of an inspection area having a high background component, i.e. a low contrast ratio and the corresponding digitized signal using a first threshold level, respectively, on a common time scale.

FIGS. 5A and 5B show a raw analog signal of an inspection area having a high background component, i.e. a low contrast ratio and the corresponding digitized signal using a second threshold level, respectively, on a common time scale.

FIGS. 9A-9D, show waveforms on a common time scale which show various steps in the processing of an analog video signal in accordance with the present invention.

DETAILED DESCRIPTION OF THE INVENTION

Figure 1:
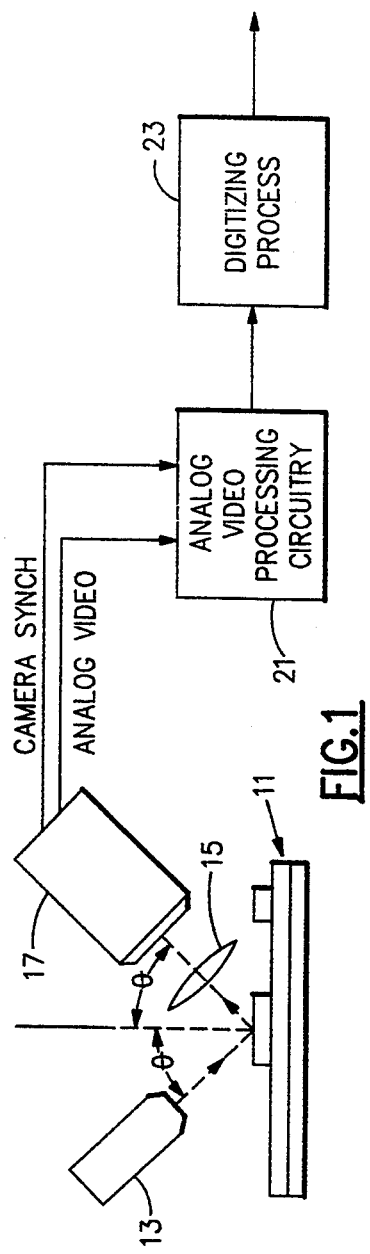
FIG. 1 is a block diagram showing an automatic optical inspection system in accordance with one embodiment of the present invention.

Referring now to the drawing wherein like elements are indicated by like reference numerals throughout, and more particularly FIG. 1 thereof, an optical image processing system for the inspection of a wide variety of printed circuit boards including subassemblies of multilayer boards including signal cores, power cores and final composites shown. Multilayer circuit board 11 is examined for the presence of reflective metal current paths creating shorts, spacing violations between conductors and missing circuit lines. The substrate can be a laminate material of any one of several different colors having different reflectivities, with more than one color present on the same board. An illumination source 13 provides white light energy at a fixed angle of incidence that scans a surface under inspection so that reflectance of this energy from the surface under inspection may be efficiently collected after passing through imaging apparatus 15 by a white light energy sensor 17 which is positioned at an angle of reflection approximately equal to the angle of incidence. The board being inspected is moved on a table under the sensor. A synchronization signal is provided which indicates when scanning occurs and when the table is being positioned between scans. In the preferred embodiment the sensor is a linear charge coupled device, which generates an analog signal for each exposed line of video by serially shifting out the signals from all charge elements of a linear array that were simultaneously exposed to the reflected light. The scanning device analog video signal and synchronization signal are connected to an analog video processing circuitry 21. The "white" and "black" levels of the analog video signal correspond respectively to the reflective and nonreflective surface areas of the image plane. This signal is changed to digital form by digitizing circuitry which forms part of the digitizing process in block 23, which can include gray scale determination so that the signal can be further processed.

Figure 2A:
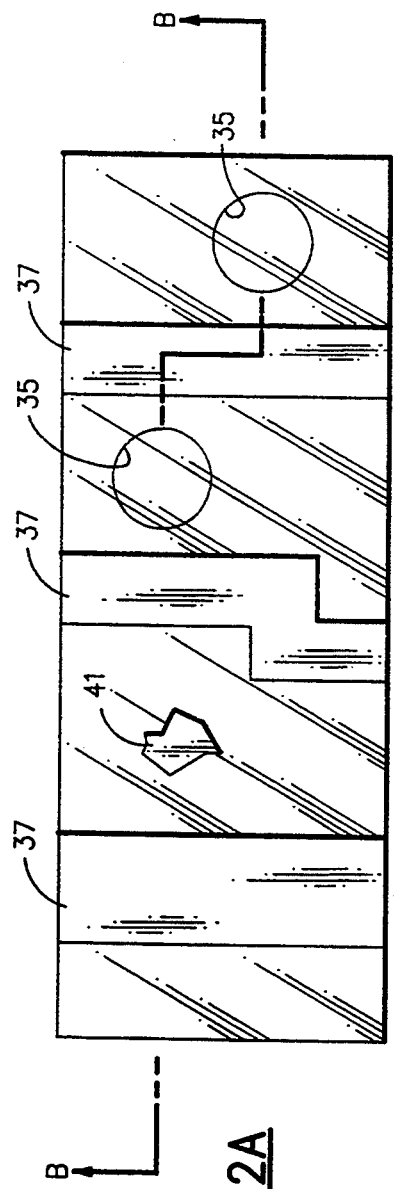
FIGS. 2A and 2B are a top view and a sectional side view taken along the line B—B, respectively, of two layers of a multilayer board where the top layer is translucent and the bottom layer is metallic.

The non-reflective or black level may vary from object-under-image to object-under-image, or within an object-under-image, due to adverse reflective surfaces resulting from oxidation, scratches, and stains. Variations in the background level are a particular problem when examining, for example, the power core portion of a multilayer board prior to drilling, having a top layer 31 of translucent laminate material and a metal layer 33 beneath with openings 35, as shown in FIGS. 2A and B. Reflective metal circuit lines 37, such as copper, gold, nickel, etc., and a metal circuit defect 41 are shown on the translucent substrate 31. Changes in the background level, caused by color differences of the bottom metallic and non-metallic areas through the translucent layer, alters the effective signal-to-noise ratio of the automated optical inspection system. As the background component changes, the process window set by the threshold level through which all image signals pass, increases the number of defect false alarms that occur due to the incorrect imaging of the background. This can limit the systems overall capability. As the background or black level, varies, digitizing thresholds become critical and typically require adjustment. These adjustments result in digitizing sensitivity tradeoffs. FIGS. 3, 4, and 5 demonstrate the effect of background level variation in the digitization process and the effect in the automated inspection process when the analog processing circuitry of the present invention is not used. Two inspection areas are sampled with an area having a low background component, that is a high contrast ratio in FIG. 3 and an area having a high background content, that is a low contrast ratio in FIGS. 4 and 5. Referring now to FIG. 3, an unprocessed analog video signal is shown in FIG. 3A and the corresponding digitized signal is shown in FIG. 3B for an inspection area having a low background component. The relative black level is indicated by reference numeral 45, and reference numeral 47 indicates the digitizing threshold. The image processing is efficiently processed and yields no false defects when the digitized signal is compared to the expected signal. Referring now to FIG. 4A, an unprocessed analog video signal for an inspection area having a high background component is shown. The surface reflection signal provided by the analog video signal yields false short defects when the corresponding digitized signal shown in FIG. 4B is compared to an expected level. If the digitizing threshold indicated by reference numeral 47 is increased as shown by reference numeral 51 in FIG. 5A, inefficient digitization again takes place as shown in FIG. 5B with the background sensitivity reduced surface sensitivity is increased resulting in false open defect being detected.

Figure 6:
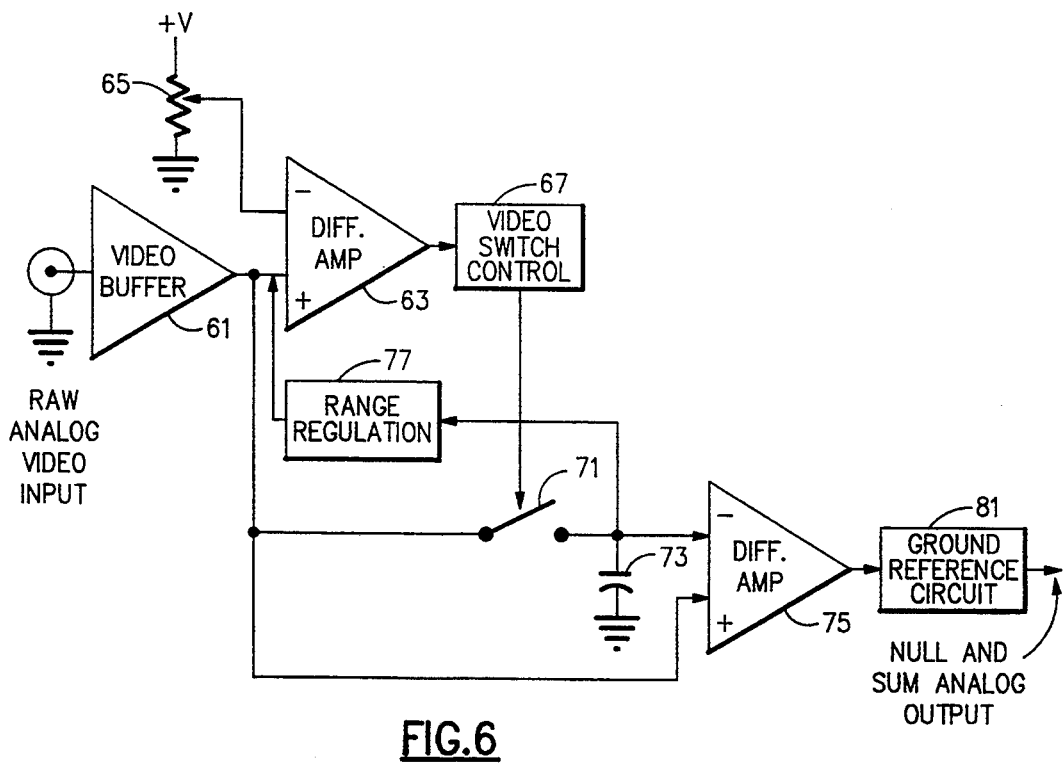
FIG. 6 is a part schematic part block diagram of the analog video processing circuitry of FIG. 1.

Referring now to FIG. 6 apparatus for processing an analog video signal prior to thresholding in accordance with the present invention is shown. The raw analog video input is passed through a video buffer 61. The output of buffer 61 is connected to the noninverting input of a differential amplifier 63 and a reference voltage from a variable resistor 65 provides the inverting input of the differential amplifier 63. The output of differential amplifier 63 is connected to one of two inputs of a video switch control 67. A camera synchronization signal from scanning device 17 is connected to the other input of video switch control 67. The output of video switch control 67 is connected to a track and hold switch 71. Switch 71 connects the output of video buffer 61 to a track and hold capacitor 73, the inverting input of a differential amplifier 75 and a range regulator 77. Differential amplifier 75 serves as a summation stage and has its noninverting input connected to the output of video buffer 61. The output of differential amplifier 75 is connected to a ground reference circuit 81 and the output of the ground reference circuit is the processed analog video signal ready for digitization.

In operation, the illumination source is adjusted to achieve a desired minimum analog video signal level from a reflective surface to be detected. The buffered analog signal from scanning device 17 is compared to a reference voltage which is set to the highest level of expected background signal in differential amplifier 63. The output of differential amplifier 63 serves as a white level detector. When a white level is detected, the video switch control 67 opens track and hold switch 71 and when a white signal is not detected, which is indicative of a background level, track and hold switch 71 is kept in the closed position. The portion of the buffered analog video signal which represents the background portion is stored by the track and hold capacitor 73. When the scanning device is between scans, track and hold switch 71 is also in the open position maintaining the background level between scans. If the background level exceeds a predetermined amount, the range regulation function reduces the magnitude of the analog video signal provided to the differential amplifier 63, which has the same effect as increasing the reference voltage level. The range regulation function operates when a background area with higher than normal reflectivity is encountered to temporarily eliminate this background without having to permanently change the reference voltage level. The background level, as represented by the voltage across capacitor 73 is subtracted from the buffered input signal in differential amplifier 75. The output of differential amplifier 75 is provided to ground reference circuit 81 and the output of the ground reference circuit is the processed analog video signal ready for gray scale processing using an A/D converter or digitization using a fixed threshold level.

The analog video processing circuit also serves to distinguish white levels from black levels based on frequency. The capacitance value of the track and hold capacitor 73 is determined by the scan rate of the scanning device and the application range. When a relatively high frequency component is detected, which implies that it is not part of the background, the signal is passed by the track and hold switch 71 to capacitor 73 since the signal amplitude was below the reference voltage level as determined by variable resistor 65. The high frequency signal is not stored by capacitor 73 and the summation results in the high frequency component not being subtracted from the buffered analog video signal.

Figure 7:
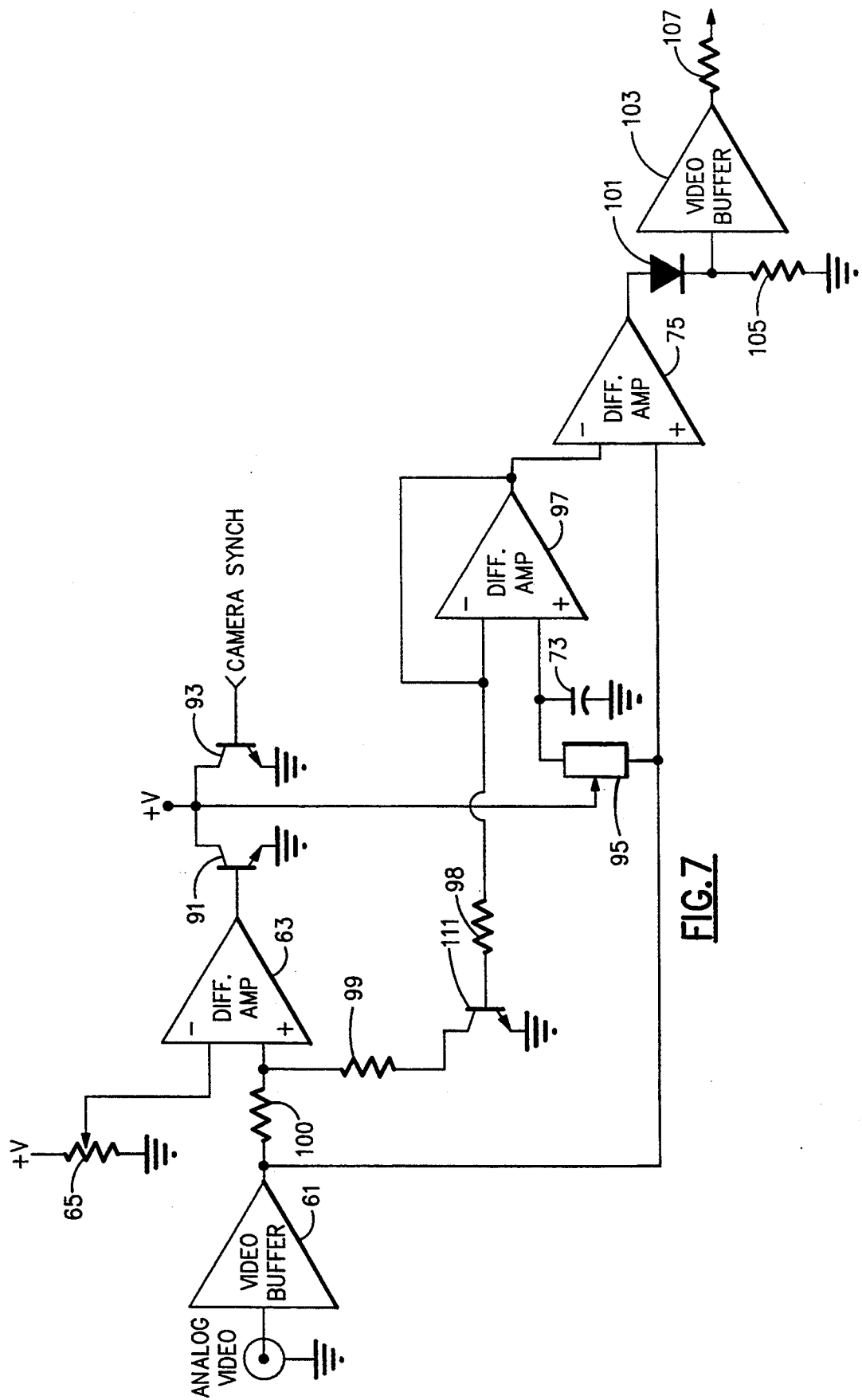
FIG. 7 is a schematic circuit diagram of the circuit of FIG. 6.

A more detailed circuit implementation of the analog video processing circuit of FIG. 6 is shown in FIG. 7. The video switch control 67 is shown as a pair of npn transistors 91 and 93 having their collectors connected to one another and connected to a power source. The output of differential amplifier 63 is connected to the base of transistor 91 and the scanner synchronization signal is connected to the base of transistor 93. The scanner synchronization signal provides a voltage during the intervals between scans. The collectors of transistors 91 and 93 are connected to the control input of a voltage controlled analog switch 95 which serves as the track and hold switch 71. When the voltage on either of the bases of the npn transistor 91 or 93 causes the transistors to conduct, the analog switch 95 is opened. A differential amplifier 97 in the follower configuration with the output connected to the inverting input, acts as a buffer between capacitor 73 and the inverting input of differential amplifier 75 providing a high input impedance and low output impedance. A diode 101, with a low forward voltage drop is connected to the input of a video buffer 103 and through a resistor 105 to ground, provides the positive difference between the analog video signal less the background level at the output of a load resistor 107 connected to the output of video buffer 103. The gain of the background level can be increased slightly compared to the gain of the video signal to compensate for the lag of the capacitor in responding to background level changes.

Range regulation is provided by an npn transistor 111 which has its base connected through a resistor 98 to the output of buffer 97. The collector of transistor 111 is connected through a voltage divider comprising series connected resistors 99 and 100 to the output of video buffer 61. Video buffer 61 is connected to the differential amplifier 63 through resistor 100. The emitter of transistor 111 is connected to ground. When the voltage on capacitor 73, which represents the background signal rises above a predetermined level, transistor 111 begins to limit the magnitude of the analog video signal provided to the differential amplifier 63 which serves as the white level detector. When transistor 111 is not conducting resistor 100 does not limit the magnitude of the signal provided by video buffer 61. When transistor begins to conduct the input signal to the differential amplifier 63 is reduced by an amount dependent on the value of resistor 99 and 100 and the voltage applied at the base of transistor 111. The resistors 99 and 100 can be selected to reduce the video buffer output provided to the differential amplifier by 33% for example when transistor is fully conductive. As can be seen in FIG. 7 the range regulator does not effect the voltage of the buffered analog video signal provided by video buffer to differential amplifier 75. The range regulation only affects the voltage level of the video signal at which the analog switch connects the unmodified video signal to the capacitor.

Video buffer 61 preferably has a fast slew rate, high current capability, and a low active impedance output which causes the capacitor voltage to follow the output of the video buffer when the capacitor is connected to the video buffer output. An example of a video buffer having these characteristics is model HA5002 manufactured by Harris Semiconductor Company. Capacitor 73 is a relatively small capacitance based on application which is able to hold the background charge when the analog switch which is turned off by the synchronization signal between scans.

Figure 2B:
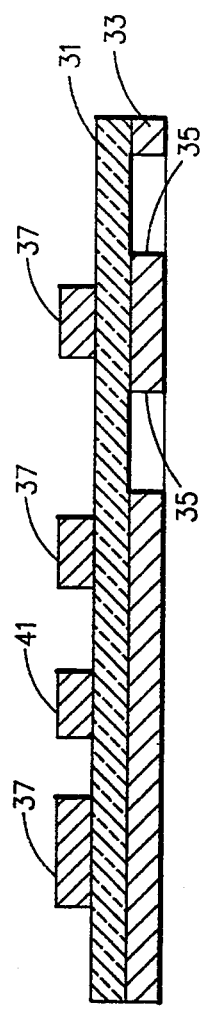
Figure 8A:
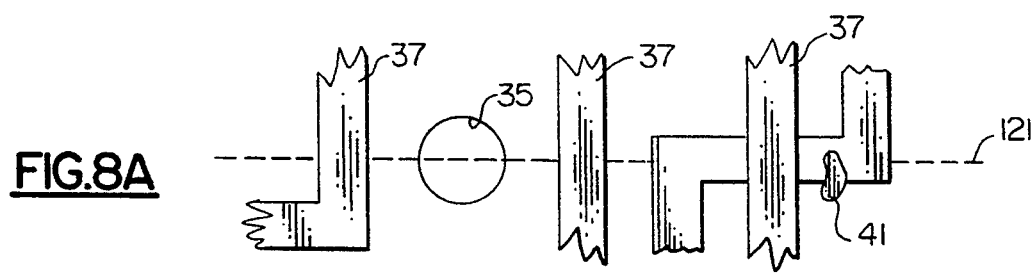
FIGS. 8A, 8B, 8C, and 8D, show a top view of a circuit board, and waveforms of the corresponding unprocessed analog video signal, the null and sum video signal provided by the analog video processing circuit of the present invention, and the resulting digital video signal, respectively.
Figure 8B:
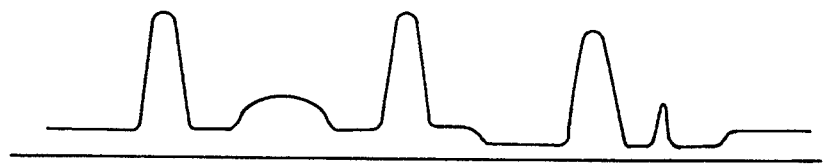
Figure 8C:
Figure 8D:
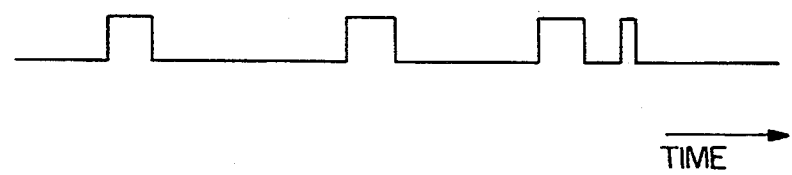

Referring now to FIGS. 8A, B, C, and D, a top view of a circuit board, and waveforms of the corresponding unprocessed analog video signal, the null and sum video signal provided by the analog video processing circuit of the present invention and the resulting digital video signal, respectively, are shown. In FIG. 8A, the line-of-video scanning path is shown by the dotted line indicated by reference numeral 121, the circuit board is of the type shown in FIG. 2 in which there is a top translucent layer and circuit patterns and holes on the layers beneath the translucent layer creating bright background areas over the hole 35 in the lower layers and darker background areas over the metallic regions on the layer beneath the translucent layer. A defect is indicated by reference numeral 41. The amplitude of the defect signal is approximately the same as the amplitude of the background signal, however due to the frequency discrimination the defect amplitude is not removed when the null and sum analog video signal is obtained as shown in FIG. 8C and therefore the defect is represented in the digital video waveform shown in FIG. 8D.

Referring now to FIG. 9 the sequence of steps in processing the analog video signals is shown. In FIG. 9A the unprocessed analog video is shown. The background level as determined by the voltage across the track and hold capacitor is shown in FIG. 9B. An inverted background level waveform is shown in FIG. 9C which is summed with original unprocessed analog video signal to provide a signal which can be digitized with a fixed threshold level without missing any defects or including defects which are not present in the circuit board being examined. Reference arrows 123 indicate a reference voltage level in each of the waveforms.

Figure 10:
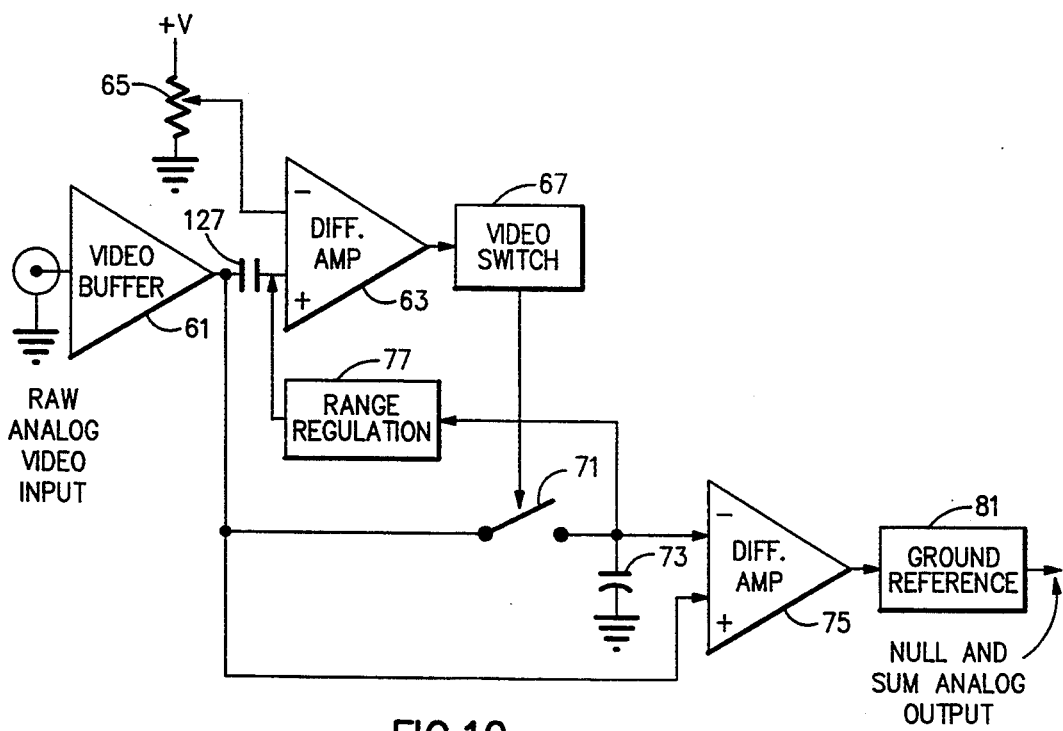
FIG. 10 is a part schematic part block diagram representation of an analog video processing circuitry in accordance with another embodiment of the present invention.

In another embodiment of the present invention as shown in FIG. 10, an analog video processing circuit is used in reverse imaging applications such as glass inspection and copier or facsimile imaging. In these applications the pertinent information is the black level and the black level needs to be made more pronounced to allow easier detection during the digitization process when thresholding levels are used. The circuitry is the same as shown in FIG. 6 with the addition of an AC coupling capacitor 127, located between the output of the video buffer 61 and the noninverting input to differential amplifier 63. The noninverting input to differential amplifier 75 is taken directly from the output of the video buffer 61 and does not pass through capacitor 127.

Figure 11A:
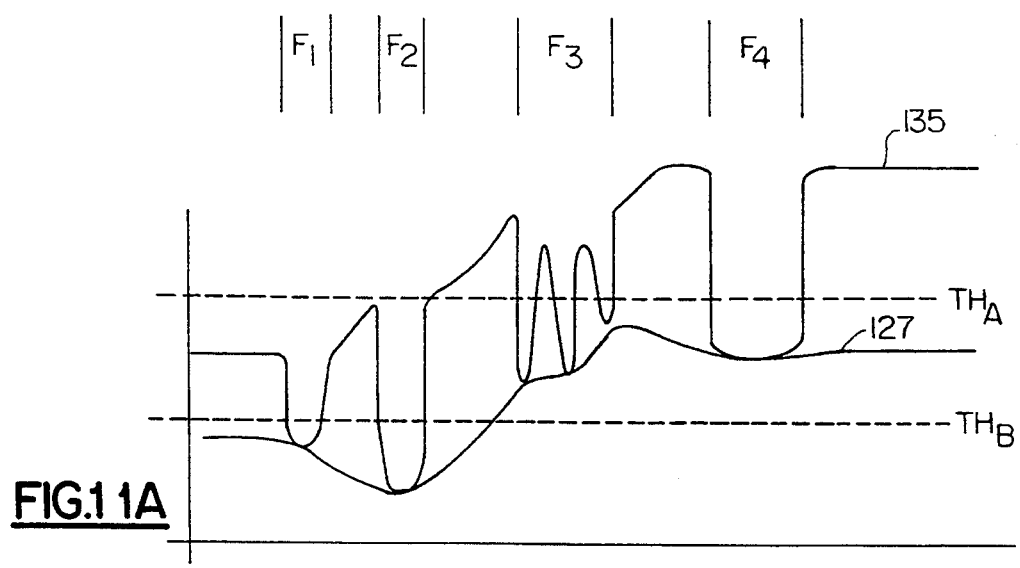
FIGS. 11A-D are waveform diagrams showing the operation of FIG. 10.
Figure 11B:
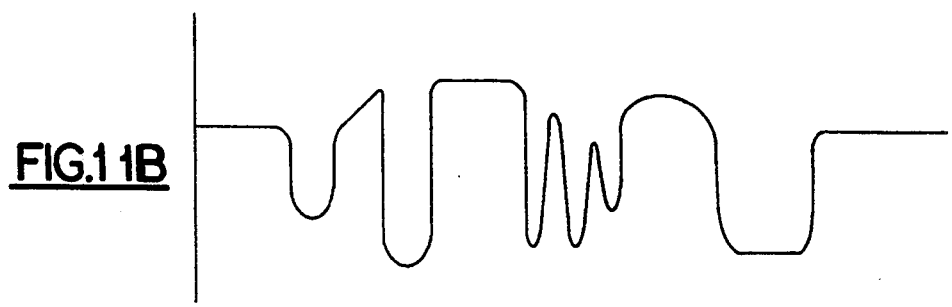
Figure 11C:
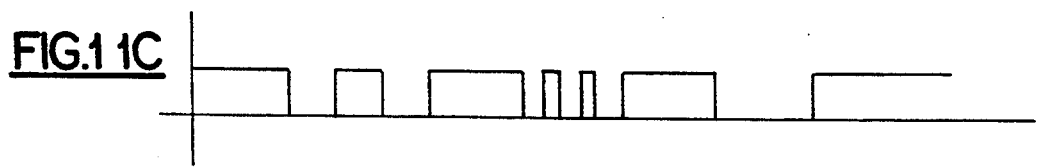
Figure 11D:
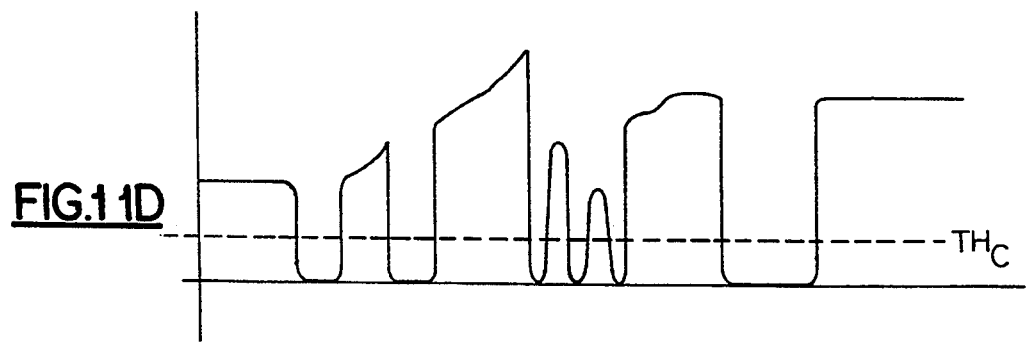

Referring now to FIG. 11A, an unprocessed signal 135 and a signal envelope 137 are shown having high frequency components. The capacitor voltage follows the lower signal envelope 137. Pertinent features which are to be detected are denoted as occurring in the time intervals F1, F2, F3, and F4 indicated between the vertical bars. Applying either threshold level Tha or Thb will not detect two of the features. The inclusion of the AC coupling capacitor 127 allows feature edge detection to be accomplished by the differential amplifier 63 shown in FIG. 11C which drives switch 71 to obtain the null and sum analog output of FIG. 11D.

The foregoing has described an analog video processing method and apparatus which enhances the signal-to-noise ratio of the analog video signal and therefore increases the digitizing sensitivity. The overall effects of background and background variations are effectively removed.

While the invention has been particularly shown and described with reference to several preferred embodiments thereof, it will be understood by those skilled in the art that various changes in form and details may be made therein without departing from the spirit and scope of the invention.

We claim:

1. An optical inspection system comprising:
   an illumination source for illuminating an object to be inspected;
   imaging apparatus responsive to light reflected from said object to be inspected for generating an analog video signal; processing means coupled to said imaging apparatus for receiving said analog video signal, including video buffer means coupled to said analog video signal for providing a buffered analog video signal; level detecting means coupled to an output of said video buffer means by ac coupling means, including means for comparing said buffered analog signal to a reference level and providing an output signal when said buffered analog signal exceeds said reference level; controllable switch means; a video switch control coupled to the output of said level detecting means for closing said controllable switch means when said buffered analog video signal does not exceed said reference level and opening said controllable switch means when said buffered analog signal does exceed said reference level; means for decreasing the magnitude of the analog signal provided to said level detecting means when said background increases above a predetermined value; track and hold means comprising a capacitor storage device coupled through said controllable switch means to said buffered analog video signal for tracking said buffered video signal when connected thereto and holding the last value when disconnected therefrom by said controllable switch means so that a background signal is developed; and summation means coupled to said track and hold means and to said video buffer for subtracting a signal proportional to the background signal from said buffered analog video signal to obtain a processed analog video signal; and analog to digital converter digitizing means for comparing said processed analog video signal to a threshold to provide a digital signal.

2. An analog video processing circuit for removing background levels comprising:
   video buffer means coupled to an analog video signal for providing a buffered analog video signal;
   level detecting means coupled to the output of said video buffer means, including means for comparing said buffered analog signal to a reference level and providing an output signal when said buffered analog signal exceeds said reference level;
   ac coupling means coupling said level detecting means to the output of said video buffer means;
   controllable switch means;
   a video switch control coupled to the output of said level detecting means for closing said controllable switch means when said buffered analog video signal does not exceed said reference level and opening when buffered analog signal does exceed said reference level;
   track and hold means comprising a capacitor storage device coupled through said switch means to said buffered analog video signal for tracking said buffered video signal when connected thereto and holding the last value when disconnected therefrom by said controllable switch means so that a background signal is developed;
   means for decreasing the magnitude of the analog video signal provided to said level detect means when said background signal increases beyond a predetermined value; and
   summation means coupled to said track and hold means and to said video buffer for subtracting a signal proportional to the background signal being tracked from said buffered analog video signal to obtain a processed analog video signal.

* * * * *